United States Patent [19]
Neuberger et al.

[11] Patent Number: 5,658,148
[45] Date of Patent: Aug. 19, 1997

[54] DENTAL LASER BRUSHING OR CLEANING DEVICE

[75] Inventors: Wolfgang Neuberger, Monchen-Gladbach, Germany; Walter Cecchetti, Padau, Italy

[73] Assignee: CeramOptec Industries, Inc., East Longmeadow, Mass.

[21] Appl. No.: 429,083

[22] Filed: Apr. 26, 1995

[51] Int. Cl.⁶ .................................................. A61C 5/00
[52] U.S. Cl. ........................ 433/215; 433/216; 433/29; 424/49
[58] Field of Search ........................ 433/216, 215, 433/29, 30, 31; 424/49-58

[56] References Cited

U.S. PATENT DOCUMENTS

| | | | |
|---|---|---|---|
| 4,743,199 | 5/1988 | Weber et al. | 433/216 |
| 4,877,401 | 10/1989 | Higuchi et al. | 433/215 |
| 5,030,090 | 7/1991 | Maeda et al. | 433/29 |
| 5,133,957 | 7/1992 | Suh et al. | 424/49 |
| 5,186,627 | 2/1993 | Amit et al. | 433/216 |
| 5,401,171 | 3/1995 | Paghdiwala | 433/215 |

FOREIGN PATENT DOCUMENTS 9011728  10/1990  WIPO ........................ 433/216

OTHER PUBLICATIONS

G. Valduga, G. Bertoloni, E. Reddi & G. Juri, "Effect of extra-cellalarly generated singlet Oxygen on Gram-positive and Gram-negative bacteria" J. Photochem. Photobiol B: Biol 22 81-6 (1993).

*Primary Examiner*—Christopher A. Bennett
*Attorney, Agent, or Firm*—Bolesh J. Skutnik; Deborah Basile

[57] ABSTRACT

The invention is an oral cleaning device incorporating a low power laser radiation source and means for producing pulsed or continuous wave delivery of low power radiation to teeth, gums and oral tissue. The device is used alone or in conjunction with a liquid jet or jets and/or with photosensitizer dental paste or liquid. The device destroys bacteria and viruses in the mouth and on surrounding tissue. It increases oral blood circulation and enhances the body's immune system response to oral infection. The device may be operated by a trained professional at three different repetition rate frequencies, selected by the operator to threat different dental conditions. The specific photosensitizer liquid or paste which is activated at a certain wavelength is chosen by the operator to treat different dental conditions. The device is also intended for home dental hygiene at low power.

13 Claims, 5 Drawing Sheets

DENTAL LASER BRUSHING OR CLEANING DEVICE

BACKGROUND OF THE INVENTION

1. Field of the Invention

The invention relates generally to a tooth and mouth cleaning or treatment instrument and to a dental liquid or paste used in conjunction with the tooth and mouth cleaning or treatment instrument.

2. Invention Disclosure Statement

Generally in the prior art mechanical cleaning of teeth with manual, electric and/or water jet devices is of a superficial nature only and does not penetrate into the skin-tissue or into pockets to remove or destroy bacteria and viral contamination. Additionally, toothpaste is of very limited effect in terms of bacterial and viral destruction. Low power laser biostimulation produces enzymes which can destroy viruses and bacteria present on teeth, in the mouth, on the gums and below the gum line. Consequential inflammation and pain is also eliminated. Radiation with pulsed diode laser at varying repetition rate frequencies is a selective trigger of the body's natural defense to infection within the mouth. Optimum effect can be achieved with GaAs (Gallium Arsenide) pulsed diode laser at a width of 200–300 nsec, $\lambda=904$ nm, power=5–10 mW, application time 1–3 minutes. Three different repetition rate frequencies can be used to treat different dental conditions as follows:

F1=73 Hz for Parodontitides, dental pain

F2=292 Hz for Gingivitis, stomatitis

F3=584 Hz for Gingivitis, stomatitis paradontophaties

It is known through research in the area of photodynamic therapy that certain substances are created as a byproduct of laser radiation. These substances contain atomic or singlet oxygen that is believed to destroy tumor cells. Similarly, atomic oxygen resulting from laser radiation can enhance destruction of oral bacteria and viruses. Research has been conducted and reported which teaches that gram-positive and gram-negative bacteria are sensitive to singlet oxygen generated by a physically separated photosensitizer. Thus, laser radiation will destroy oral bacteria. [See, e.g., Giuliana Valduga et. al., "Effect of Extracellularly Generated Singlet Oxygen on Gram-positive and Gram-negative Bacteria," *J. Photochem. Photobiol. B. Biol.*, 21 (1993) 81–86.]

The wavelength at which the diode laser of the device is operated is related to the specific photosensitizer used. A photosensitizer such as a Phthalocyanine can be activated by continuous wave diode laser as follows:

(a) Zn (II) phthalocyanine is activated at $\lambda=670$ nm (b) Si (IV) naphthalocyanine is activated at $\lambda=780$ nm (c) Pd (OBu)$_8$ naphthalocyanine is activated at $\lambda=820$ nm

BRIEF SUMMARY OF THE INVENTION

It is an aim of the present invention to address the need for an oral cleaning or treatment device which will have a significant destructive effect on bacteria and viruses.

It is a further aim of the present invention to provide a device to permit the delivery of low power radiation through the bristles of a toothbrush.

It is yet another aim of the present invention to provide a device to permit the delivery of low power radiation through a liquid jet or jets within the device.

It is also an aim of the present invention to provide a device that permits the delivery of low power radiation directly from a low-power small radiator such as a diode-laser to areas of the oral areas to be treated or cleaned.

It is additionally an aim of the current invention to provide a device that may be used separately from a cleaning device if desired, and that may provide variable treatment combinations by the selection of switches that control the radiation source, and that may provide sanitary, disposable treatment or cleaning portions of the device to allow multiple users to take advantage of the device.

It is a yet a further aim of the present invention to provide a cleaning material defined as a toothpaste or liquid to be used with the oral cleaning device which is radiation activated at certain wavelengths.

An object of the invention is to respond to the need for an inexpensive, consumer-oriented hand-held tooth and mouth cleaning device which will emit low-power laser radiation for in-home treatment of oral infections, gingivitis and periodontal disease and for use by dentists and oral surgeons in preparation for surgery, in treatment of oral infection or during oral surgical procedures. Used in conjunction with the radiation activated toothpaste or liquid the effect on oral inflammation and infection is significant.

Briefly stated, in the present invention an oral cleaning device using low power radiation is provided which enhances destruction of oral viruses and bacteria, increases blood circulation and thereby increases the body's immune system response to the oral infection. The present invention teaches a device which will have a significant effect on the treatment of all types of oral diseases, inflammations, and infections.

As an alternative to a pulsed diode laser, a continuous wave diode laser can be used with or without a photosensitizer liquid for selective biostimulation.

Low power laser radiation also increases blood circulation to maintain dental and gum health. The invention addresses these needs by teaching a consumer oriented device combining the benefits of mechanical cleaning with tissue penetration and virus/bacterial elimination using low power radiation delivered with either a pulsed or continuous wave mode.

The invention also teaches a photosensitizer dental liquid or paste to be used with the dental laser brush device which is activated by a laser wavelength. The photosensitizer toothpastes or liquid supplements increases the effectiveness of the laser assisted cleaning instrument.

The above, and other objects, features and advantages of the present invention will become apparent from the following description read in conjunction with the accompanying drawings.

DETAILED DESCRIPTION OF THE PREFERRED EMBODIMENT(S)

Figure 1:
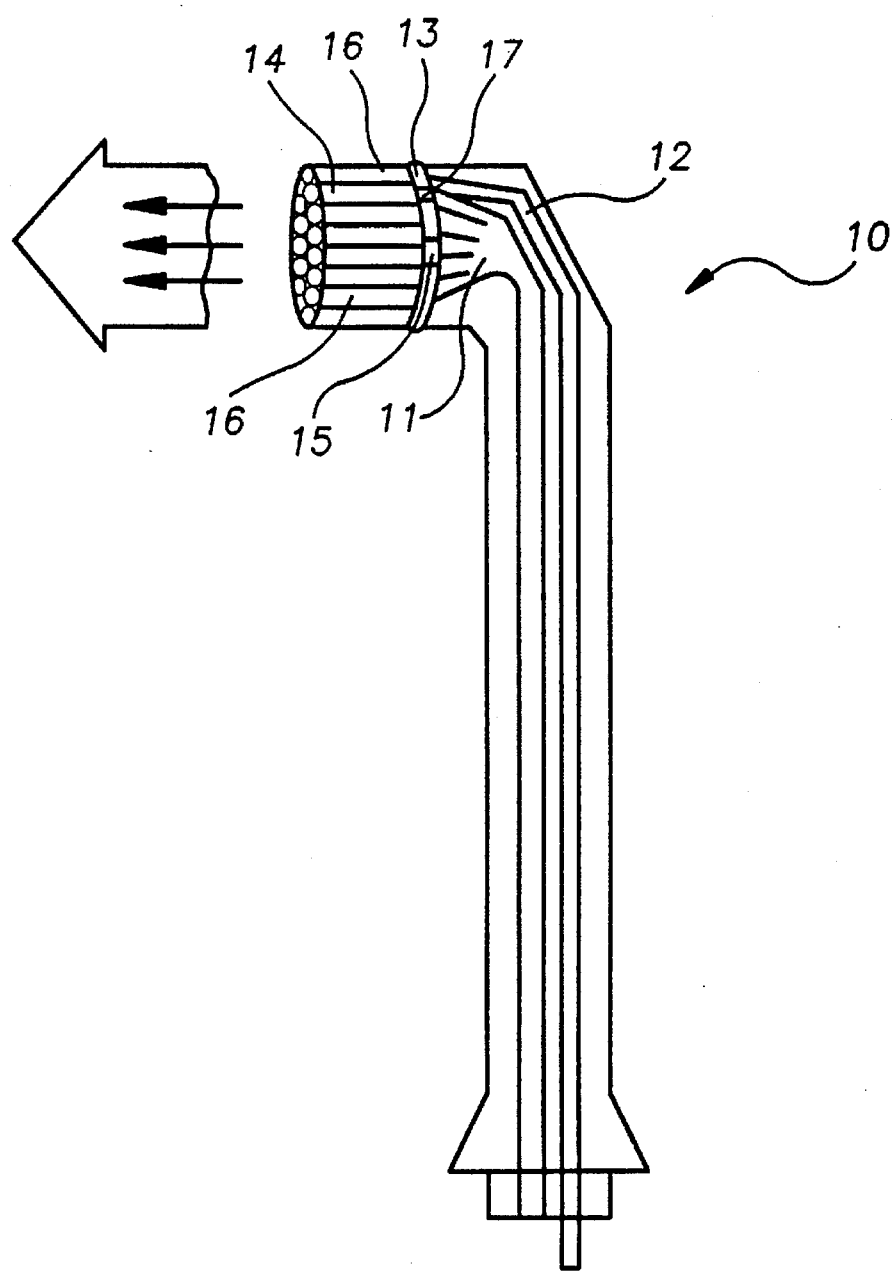
FIG. 1 is a view if the end of the mechanical oral cleaning device showing a circular fixed tip, optical fibers and liquid jets within the brushhead for laser radiation delivery.

FIG. 1 shows a preferred embodiment of the invention in which plastic brush 10 can be manufactured in a multiplicity of colors and is removable from a handle. Plastic brush 10 contains one or more optical fiber 11s and water or liquid passage 12. Optical fiber 11(s) carry radiation from a radiation source to brushhead 13, and water or liquid passage 12 carries water or liquid under pressure to brushhead 13. Optical fiber 11(s) may be optically connected to one or more optical bristle 14s, which deliver radiation to the areas in the mouth being cleaned through bristle 14 end not optically connected to optical fiber 11(s). Optical fiber 11(s) may also terminate in one or more optical opening 15(s) located in brushhead 13, delivering radiation from optical opening 15(s) to the oral areas being cleaned via the air gap between them. Radiation may also be delivered using passage 12, which terminates in brushhead 13 by being connected to one or more hollow bristle 16(s) or one or more liquid opening 17(s).

Figure 2:
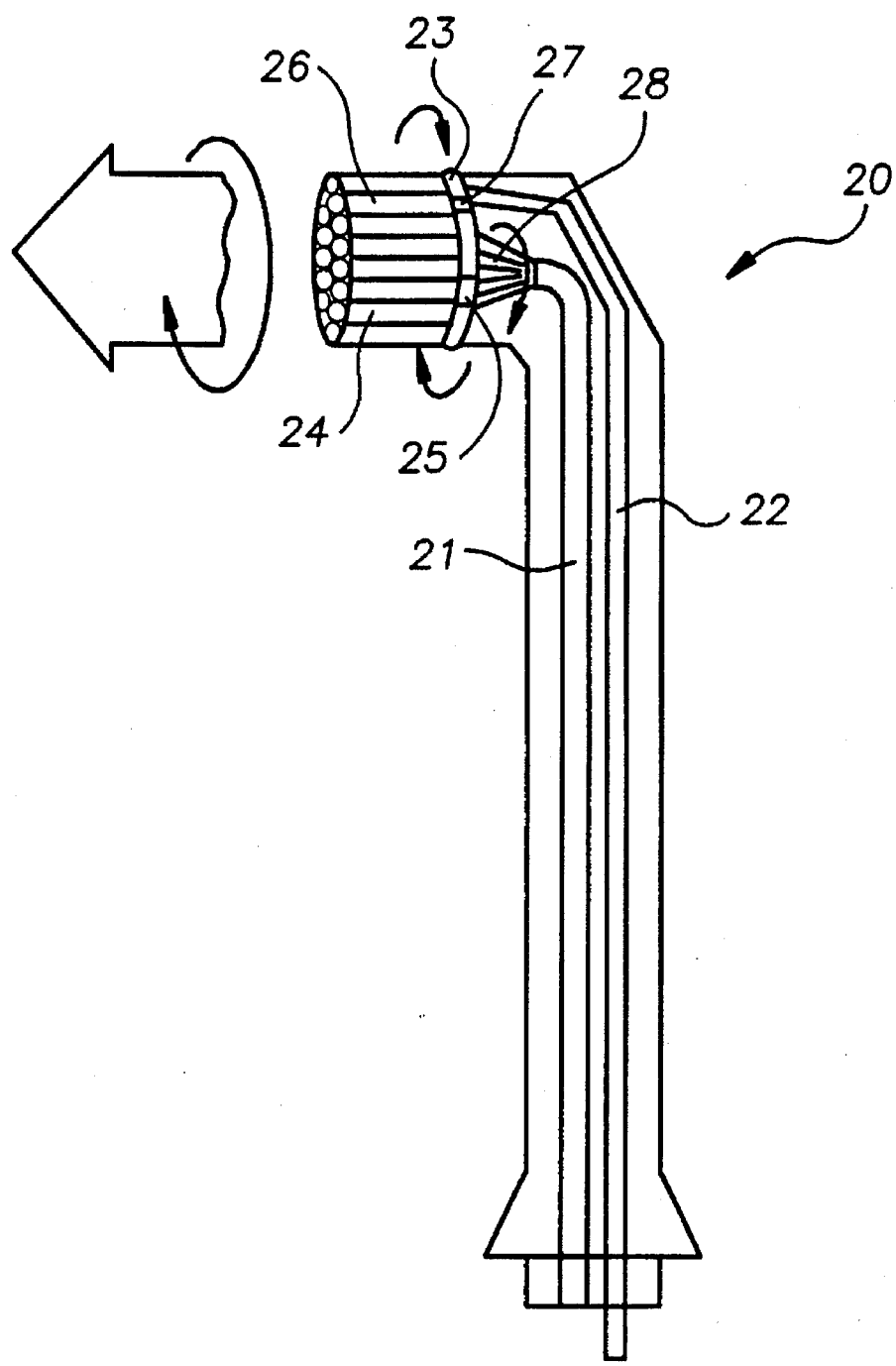
FIG. 2 is a view of the end of a mechanical oral cleaning device showing a circular rotating tip, optical fibers and liquid jets within the neck of the device for broader laser radiation delivery.

FIG. 2 shows another preferred embodiment of the invention in which plastic brush 20 can be manufactured in a multiplicity of colors, is removable from a handle, and has rotatable brushhead 23. Plastic brush 20 contains one or more optical fiber 21(s) and water or liquid passage 22. Optical fiber 21 (or each optical fiber 21) carries radiation from a radiation source to rotatable optical connection 28, and water or liquid passage 22 carries water or liquid under pressure to rotatable brushhead 23. Optical fiber 21(s) may be optically connected to one or more optical bristle 24s via optical connector 28, which deliver radiation to the areas in the mouth being cleaned through bristle 24 end not optically connected to optical connector 28. Optical fiber 21(s) may also terminate in one or more optical opening 25(s) located in rotatable brushhead 23, delivering radiation from optical opening 25(s) to the oral areas being cleaned via the air gap between them. Radiation may also be delivered using a liquid going through passage 22. Passage 22 terminates at rotatable brushhead 23 and is connected to one or more hollow bristle 26(s) or one or more liquid opening 27(s). The liquid is delivered to the area to be cleaned or treated by passing through one or more hollow bristle 26(s) or one or more liquid opening 27(s).

Radiation is delivered by a pulsed diode laser or a continuous wave diode laser, to exactly where it is needed through plastic brush tips 10 or 20 in the normal course of tooth brushing. The present invention in these embodiments incorporates the properties of simple laser biostimulation which produces enzymes which remove and reduce the byproducts of tissue inflammation and thereby reduce swelling and assist to alleviate pain in the inflamed tissue.

Figure 3:
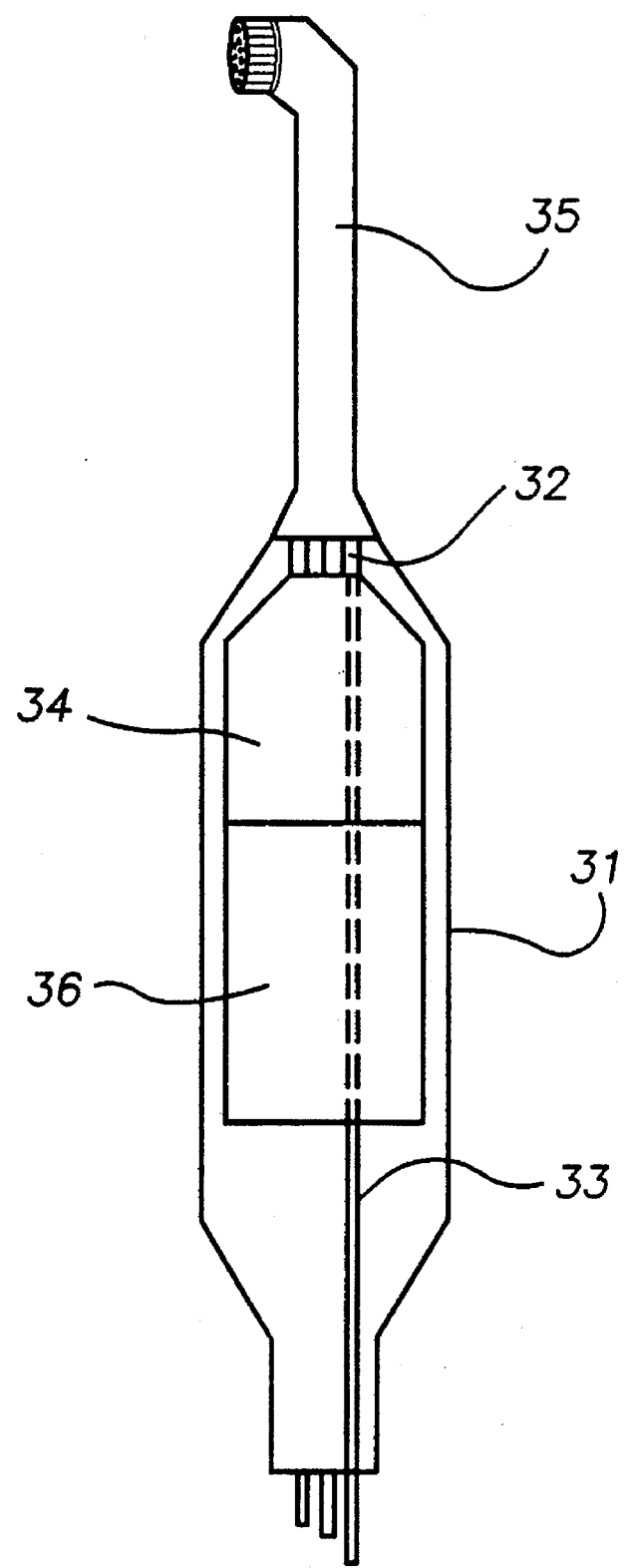
FIG. 3 is a sectional view of the mechanical oral cleaning device showing a brushhead, diode laser, power supply, cooling means and driver.

FIG. 3 shows handle means 31 containing diode laser 32 and electrical wiring 33, and cooling means 34 consisting of a Peltier cell. Radiation from diode laser 32 is delivered through replaceable brush 35. Handle means 31 may also contain battery cell or cells 36 which power diode laser 32.

Figure 4:
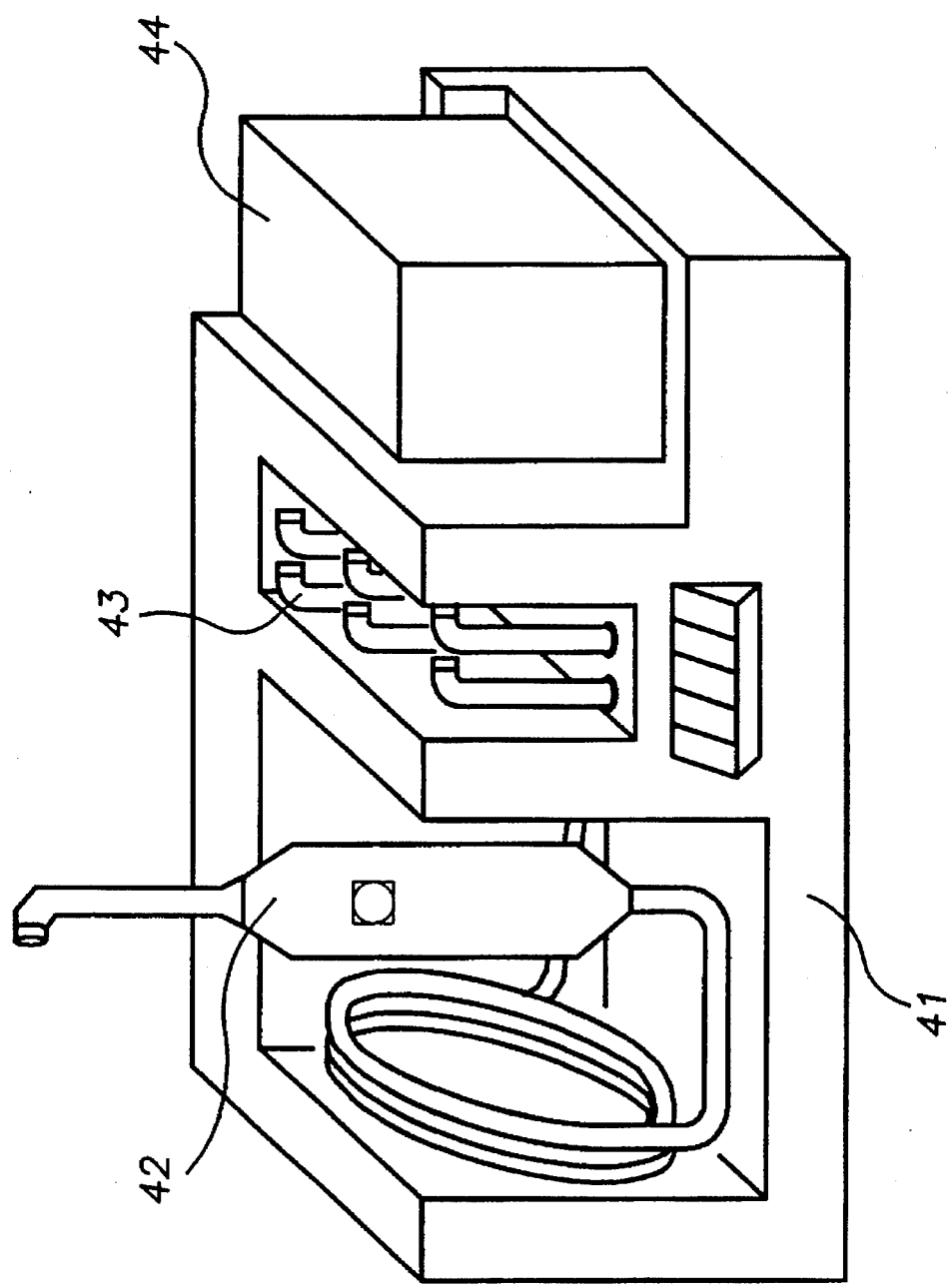
FIG. 4 shows a mechanical oral cleaning device placed within a console having a colored, replacement brush tips, means for a dental liquid dispenser and electrical components.

FIG. 4 shows the mechanical oral cleaning device placed within console 41 whereby the handle means 42 enclosing a diode laser is secured and replacement brushes 43 are easily accessible. Console 41 also contains container 44 for storage of the dental or photosensitizer liquid or paste. Console 41 contains within its structure a sufficient length of cable for use of the brushing device in dental surgery or for any other application. Console 41 also contains within its structure a micropump for any liquid under pressure that may be needed and all needed electrical circuits.

Figure 5:
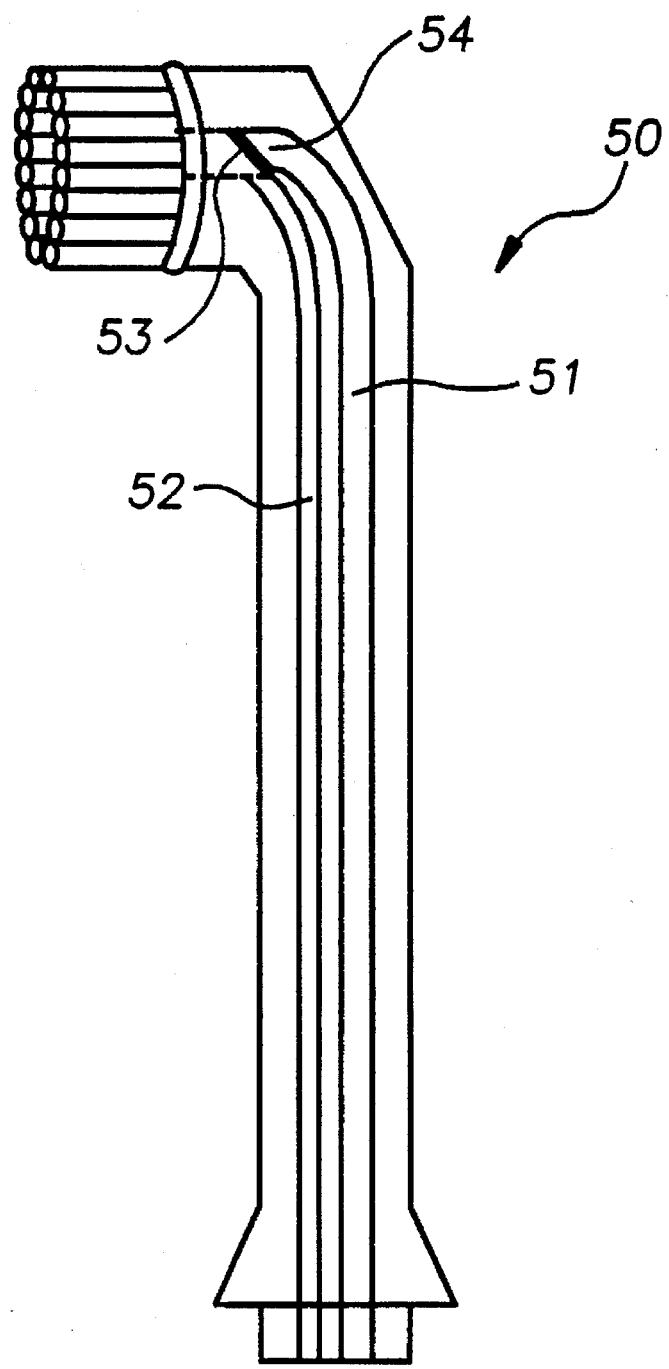
FIG. 5 is a view of a mechanical oral cleaning device with an optical fiber and a liquid jet, where the fiber optic's end terminates in at a safety-designed angle.

FIG. 5 shows a preferred embodiment of the invention in which plastic brush 50 can be manufactured in a multiplicity of colors and is removable from a handle. Plastic brush 50 contains optical fiber 51 and water or liquid passage 52. Optical fiber 51 carries radiation from a radiation source to fiber end 53, which terminates at designated angle 54 relative to optical fiber 51's longitudinal axis. Water or liquid passage 52 carries water or liquid under pressure to fiber end 53. Water or liquid passes through passage 52, over surface of fiber end 53, and then through liquid and laser radiation delivery opening 55 to any proximal oral area to be cleaned or treated. Plastic brush 50 is designed to be safe for home use by the fact that laser radiation coming to fiber end 53 will be reflected harmlessly upward into plastic brush 50 if no liquid is being forced through liquid passage 52. This is due to angle 54 which creates a reflective surface because air and optical fiber 51 have substantially different n. When liquid is passing over the surface of fiber end 53 laser radiation will pass through substantially parallel to the longitudinal axis of optical fiber 51, thereby being delivered to oral areas to be cleaned or treated via opening 55 with the liquid that came through passage 52. This occurs because the difference in n between optical fiber 51 and a liquid or water is low enough that fiber end 53 is now a refractive, rather than a reflective, surface.

In the present invention, the dental laser brushing device can be used in combination with a photosensitizer toothpaste or liquid which is applied to the bristles of the device. The photosensitizer liquid or paste when activated by an appropriate laser wavelength produces hyperactive singlet oxygen that destroys bacteria. The method is similar to photodynamic therapy of tumors in which the photosensitizer releases singlet oxygen that destroys tumor cells. The present invention uses low power laser energy delivered by pulsed or by continuous wave action and a low concentration of photosensitizer for consumer use. The dental laser brushing device may be used in connection with oral surgery at a medium laser energy delivery and using a specific concentration of photosensitizer liquid. The present invention guarantees good penetration of oral tissues.

The low power radiation can be delivered at three (3) different frequencies which can be selected by the operator based upon the particular treatment to be rendered and the particular photosensitizer liquid used. The result is photodynamic therapy whereby the selection of diode laser wavelength is related to the type of treatment to be conducted.

In a preferred embodiment of the invention and as shown in the drawings, the diode laser can be incorporated into the handle of the device together with its power supply and if necessary, with Peltier cells as a cooling system. Radiation from a diode laser source is delivered through one or more of the bristles on a replaceable brush that has a fixed or rotatable brushhead, or through liquid jets, or through openings in the brushhead corresponding to the radiation delivery medium. The diode laser will run on the battery or battery cells inside the handle. The replaceable brushes have one of two types of brushheads:

(a) rotating bristles which are activated by applying the bristles to the oral surface or by the pressure of the flow of liquid through the jets;

(b) fixed bristles which are activated by applying the bristles to the oral surface or by the pressure of the flow of liquid through the liquid jets.

The rotating motion of the bristles, the pulsing action of the pulsed delivery, and/or the pressure of the liquid jets all increase the effectiveness of the device.

Also in a preferred embodiment of the invention, the handle containing the diode laser is linked to a console by cable where there are electrical wires and small tubing for delivery of the dental liquid. The console contains all the necessary electronic components for operation of the dental laser brushing device. The console contains a container to hold the dental liquid or paste and its micropump. This dental liquid can be a toothpaste, a pharmacological substance for medical treatment and/or a photosensitizer liquid for photodynamic-like therapy.

Various replacement brushes can be inserted into the handle with an easy snap connection that guarantees optical connection between the diode laser and the optical fiber in the brush, and between the tubing that delivers the dental liquid to the tubing in the brush. The brushes may be different colors for easy individual identification by multiple users within a family. The brushes may also be sterilized for professional use by dentists and oral surgeons.

Also, in the preferred embodiment the laser radiation from diode laser source is delivered through the brushhead together with a liquid jet. Alternatively, the liquid jet itself can be the optical transfer medium for the radiation as the refractive index of water or the liquid is higher than that of air and as it is reasonably transparent for certain wavelengths applications to the procedure.

Having described the preferred embodiment of the invention with references to the accompanying drawings, it is to be understood that the invention is not limited to that precise embodiment and that various changes and modifications may be effected therein by one skilled in the art without departing from the scope or spirit of the invention as defined in the appended claims.

What is claimed is:

1. A cleaning device to clean teeth, gums and other oral areas comprising:

a handle, a brushhead, a radiation source, and a power source for said radiation source;

said brushhead further comprising a backing plate and a multiplicity of bristles;

said radiation source being a diode laser a delivery means for said radiation;

said delivery means for said radiation comprising an optical fiber optically connected to said radiation source;

said optical fiber being terminated such that said optical fiber's longitudinal axis is substantially directed at an opening in said brushhead;

said opening allowing passage of a liquid and radiation to oral areas to be cleaned;

a tube providing passage for liquid under pressure;

said optical fiber having a termination-tip which forms a substantially flat surface relative to said optical fiber's longitudinal axis;

said tube having an open-end substantially near said termination-tip;

said liquid coming through said open-end passing over said surface of said termination-tip;

an angle formed between said surface of said termination tip and said optical fiber's longitudinal axis forming a substantially refractive surface for said radiation while liquid is passing over said surface and then to said opening thereby passing said radiation substantially through said opening; and said angle forming a substantially reflective surface for said radiation when said liquid is not passing over said surface, thereby passing said radiation substantially to said brushhead.

2. A cleaning device according to claim 1 wherein said diode-laser is enclosed in said handle.

3. A cleaning device according to claim 1 wherein at least said brushhead is considered disposable.

4. A cleaning device according to claim 1 further comprising an interlocking means for controlling the delivery of said radiation.

5. A cleaning device according to claim 1 further comprising means to deliver and select different radiation frequencies for treatment of a particular oral infection or condition.

6. A treatment device to treat teeth, gums and other oral areas comprising:

a handle, a brushhead, a radiation source, and a power source for said radiation source;

said brushhead further comprising a backing plate and a multiplicity of bristles;

said radiation source being a diode laser a delivery means for said radiation;

said delivery means for said radiation comprising an optical fiber optically connected to said radiation source;

said optical fiber being terminated such that said optical fiber's longitudinal axis is substantially directed at an opening in said brushhead;

said opening allowing passage of a liquid and radiation to oral areas to be cleaned;

a tube providing passage for liquid under pressure;

said optical fiber having a termination-tip which forms a substantially flat surface relative to said optical fiber's longitudinal axis;

said tube having an open-end substantially near said termination-tip;

said liquid coming through said open-end passing over said surface of said termination-tip;

an angle formed between said surface of said termination tip and said optical fiber's longitudinal axis forming a substantially refractive surface for said radiation while liquid is passing over said surface and then to said opening thereby passing said radiation substantially through said opening; and said angle forming a substantially reflective surface for said radiation when said liquid is not passing over said surface, thereby passing said radiation substantially to said brushhead.

7. A treatment device according to claim 6 wherein said diode laser is enclosed in said handle.

8. A treatment device according to claim 6 wherein at least said head is considered disposable.

9. A treatment device according to claim 6 further comprising an interlocking means for controlling the delivery of said radiation.

10. An oral treatment device according to claim 6 further comprising means to deliver and select different radiation frequencies for treatment of a particular oral infection or condition.

11. A dental liquid or paste containing photosensitizer substances, having specific absorption wavelengths and which on being irradiated at said wavelength create singlet oxygen in the immediate vicinity of said liquid or paste.

12. A method of treatment for teeth, gums, and other oral areas comprising the steps of:

applying to a preselected oral area, a liquid/paste containing photosensitizer substances as given in claim 11;

irradiating said preselected oral area with said specific absorption wavelength and thereby creating singlet oxygen as an active species;

having said singlet oxygen react with surfaces within said preselected oral area; and rinsing away any residue after reaction of said singlet oxygen and said surfaces.

13. The method of treatment according to claim 12, further comprising the step of:

selecting a frequency for delivery of said specific absorption wavelength based on the specific dental treatment undertaken and on which specific photosensitizer substances are present in said liquid/paste.

* * * * *